(12) United States Patent
Badoux et al.

(10) Patent No.: US 8,076,929 B2
(45) Date of Patent: Dec. 13, 2011

(54) DEVICE AND METHOD FOR DETECTING AN ANOMALY IN AN ASSEMBLY OF A FIRST AND A SECOND OBJECT

(75) Inventors: Dave Badoux, Amsterdam (NL); Paulus Carolus Nicolaas Crouzen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 306 days.

(21) Appl. No.: 12/441,997

(22) PCT Filed: Sep. 20, 2007

(86) PCT No.: PCT/EP2007/059949
§ 371 (c)(1),
(2), (4) Date: Mar. 19, 2009

(87) PCT Pub. No.: WO2008/034867
PCT Pub. Date: Mar. 27, 2008

(65) Prior Publication Data
US 2010/0045279 A1 Feb. 25, 2010

(30) Foreign Application Priority Data

Sep. 21, 2006 (EP) .................................. 06121041
Sep. 21, 2006 (EP) .................................. 06121044

(51) Int. Cl.
*G01R 33/12* (2006.01)
(52) U.S. Cl. ..................................................... 324/228
(58) Field of Classification Search .................. None
See application file for complete search history.

(56) References Cited

U.S. PATENT DOCUMENTS

| 3,693,075 A | 9/1972 | Förster ............................. 324/40 |
| 3,940,689 A | 2/1976 | Johnson, Jr. ...................... 324/37 |
| 4,188,577 A | 2/1980 | Mhatre et al. .................. 324/220 |
| 4,701,892 A | 10/1987 | Anderson ........................ 367/35 |
| 4,715,442 A | 12/1987 | Kahil et al. ..................... 166/250 |
| 5,124,641 A | 6/1992 | Netter et al. ................... 324/230 |
| 5,670,878 A * | 9/1997 | Katahara et al. ............... 324/221 |
| 6,131,659 A | 10/2000 | Johnson .................... 166/250.05 |
| 6,291,992 B1 * | 9/2001 | van Andel et al. ............. 324/240 |
| 6,538,435 B2 * | 3/2003 | Crouzen et al. ................ 324/232 |
| 6,570,379 B2 * | 5/2003 | Crouzen et al. ............... 324/240 |

(Continued)

FOREIGN PATENT DOCUMENTS

EP          321112          6/1989

(Continued)

*Primary Examiner* — Jermele M Hollington
(74) *Attorney, Agent, or Firm* — William E. Hickman

(57) ABSTRACT

A method for detecting an anomaly in an assembly of a first and a second object of electrically conductive material forming an intermediate space between them, comprising providing a device (5) comprising a transmitter/receiver arrangement (7) for generating an electromagnetic field, and for measuring a signal indicative of an eddy current which is generated in the assembly by the electromagnetic field; arranging the device in a measurement position within the intermediate space; activating the device so as to receive a signal indicative of an eddy current in the assembly; and comparing the signal with a norm so as to detect if an anomaly is present at the measurement position, and a device for detecting an anomaly in an assembly of a first and a second object forming an intermediate space between them, the device comprising a transmitter/receiver arrangement a fixation means which. is arranged to fix the transmitter/receiver arrangement at a measurement position with respect to the inspection object.

20 Claims, 6 Drawing Sheets

U.S. PATENT DOCUMENTS

| | | | |
|---|---|---|---|
| 6,707,296 B2 * | 3/2004 | Looijer | 324/240 |
| 2002/0097045 A1 * | 7/2002 | Crouzen et al. | 324/240 |
| 2009/0242200 A1 * | 10/2009 | Badoux et al. | 324/239 |

FOREIGN PATENT DOCUMENTS

| | | |
|---|---|---|
| EP | 910784 | 5/2002 |
| EP | 1576335 | 9/2005 |
| EP | 1478899 | 12/2005 |
| GB | 2262346 | 6/1993 |
| WO | WO9500839 | 1/1995 |
| WO | WO0216863 | 2/2002 |
| WO | WO0216921 | 2/2002 |
| WO | WO0216923 | 2/2002 |

* cited by examiner

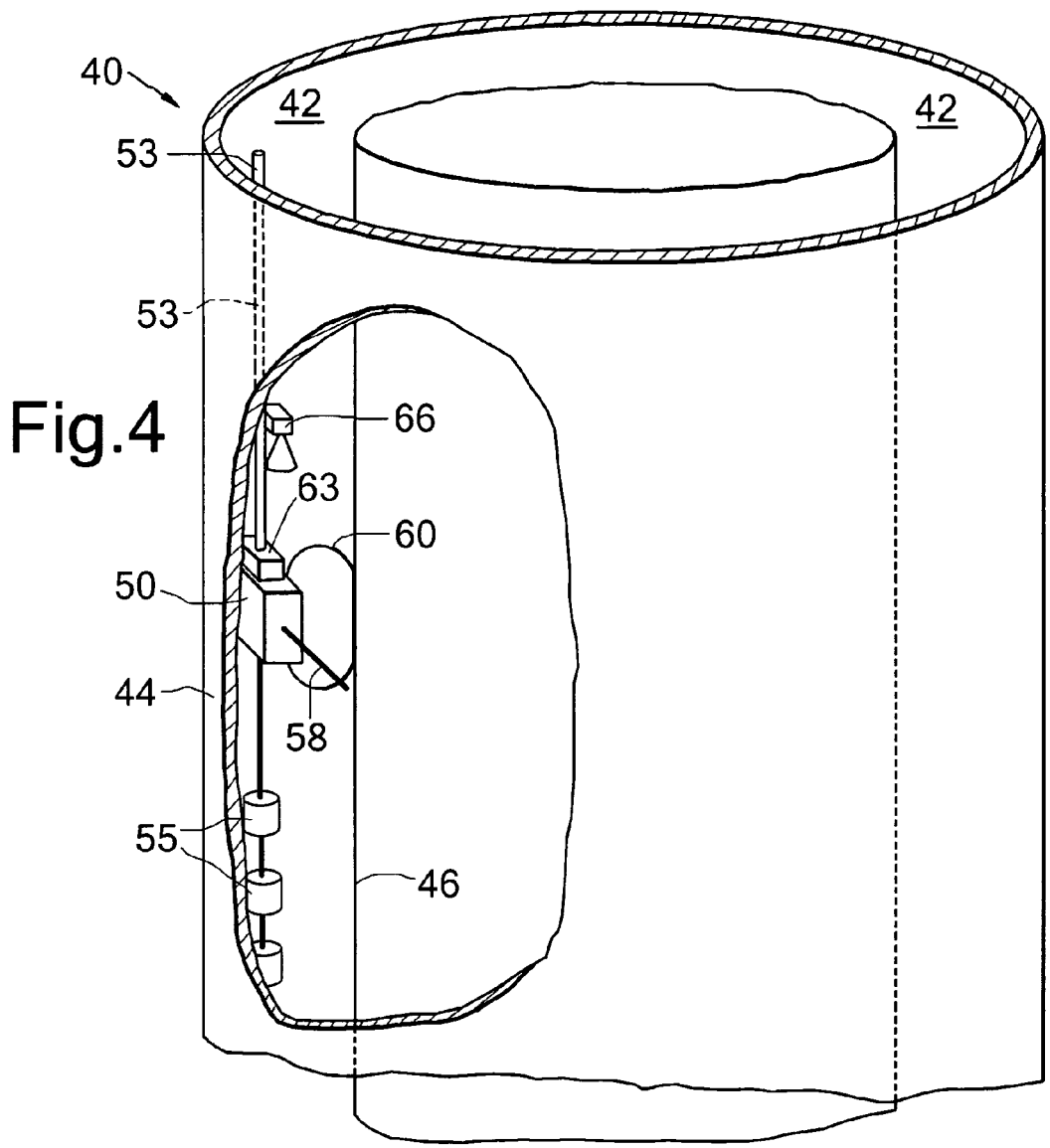
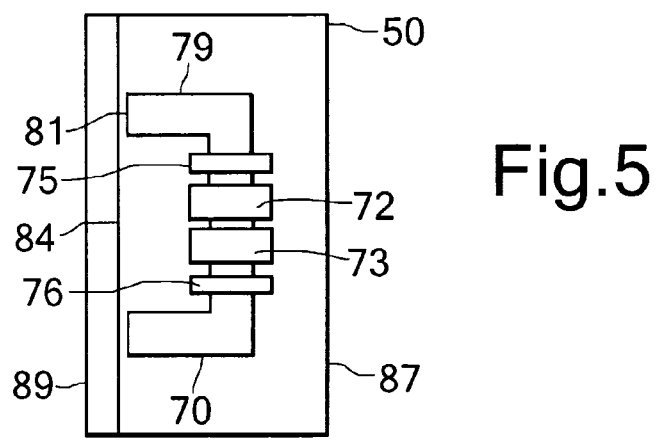

DEVICE AND METHOD FOR DETECTING AN ANOMALY IN AN ASSEMBLY OF A FIRST AND A SECOND OBJECT

The present application claims priority of European Patent Applications Nos. 06121041.5 filed 21 Sep. 2006 and 06121044.9 filed 21 Sep. 2006.

FIELD OF THE INVENTION

The present invention relates to a method and device for detecting an anomaly in an assembly of a first and a second object forming an intermediate space between them.

BACKGROUND OF THE INVENTION

Hydrocarbon wells are typically completed with an assembly of concentric steel pipes, referred to as conductors, casing, or tubing. The completion extends from a wellhead downwardly into the wellbore. The wellhead can be at land, or in offshore installations at a platform. Several parts of the completion can be subject to corrosion. In offshore installations for example, sea water can be present in an outer annulus of a completion, such as between a conductor and the outer casing. Corrosion sensitive areas are at sea level, where tidal effects and waves cause exposure of the well completion to water and air, or in a so-called splash zone even to aerated water. There is a need to perform inspection of such completions.

Inspection of well casing by passing a tool centrally down a tubular or casing is known from e.g. specification U.S. Pat. No. 4,701,892. Such inspection tools interfere with production of hydrocarbons, however. If it is known beforehand that corrosion inspection is desired, a fixed downhole corrosion monitoring apparatus comprising piezoelectric transducers as known from U.S. Pat. No. 6,131,659 can be installed. If fixed equipment is not present and if production is not to be disturbed, oftentimes the only practical access path is through the open annulus between tubulars.

An option in this case is visual inspection by passing video equipment down the annulus, but there is a need for a more precise inspection method that can spot anomalies that can compromise the integrity of steel objects, e.g. a significant wall thickness decrease with respect to a norm. Apart from well completions, similar problems are also encountered in other situations where two metal objects, in particular steel objects have to be inspected from a narrow intermediate space between them.

SUMMARY OF THE INVENTION

To this end the present invention provides a method for detecting an anomaly in an assembly of a first and a second object of electrically conductive material forming an intermediate space between them, the method comprising
  providing a device comprising a transmitter/receiver arrangement for generating an electromagnetic field, and for measuring a signal indicative of an eddy current which is generated in the assembly by the electromagnetic field;
  arranging the device in a measurement position within the intermediate space;
  activating the device so as to receive a signal indicative of an eddy current in the assembly; and
  comparing the signal with a norm so as to detect if an anomaly is present at the measurement position.

Methods for inspecting an electrically conductive object by means of eddy current measurements, in particular transient eddy currents, are known in the art. Analysis of the electromagnetic signature of eddy currents induced into an electrically conductive object yields information about anomalies in the inspected object, e.g. wall thickness variations can be measured, cracks or surface defects can be located. For applications between two electrically conductive objects, in particular between two steel objects such as in an annulus formed by tubulars of a well completion, eddy current measurements would however not have been considered in the past.

One reason is that the eddy current probe would generate eddy currents in and pick up eddy current signatures from both objects. The invention is partly based on the insight, that it is in many cases not needed to distinguish between the two objects. Rather it can be sufficient to identify the location of an anomaly, which can be on either one of the objects, or both. The first and second objects can in particular be an inner and an outer tubular with an annulus as intermediate space between them, in particular wherein the inner and outer tubulars form part of a well completion.

So, the present invention provides the use of a device comprising a transmitter/receiver arrangement for generating an electromagnetic field in an electrically conductive object, and for measuring a signal indicative of an eddy current which is generated in the assembly by the electromagnetic field for inspecting an assembly of a first and a second object of electrically conductive material second for the presence of an anomaly.

An anomaly is a deviation from an expected or desired status of the inspected assembly of two objects. The expected or desired status is characterized by one or more parameters, such as two wall thicknesses, and gives rise to a response of the assembly to an eddy current inspection. The expected or desired response is referred to as the norm, the norm can also cover a range of expected and desired responses. It can for example be determined on a part of the assembly, which is without anomalies, or it can be predicted such as by making use of a calibration or extrapolation or interpolation from measurements on similar objects.

Often pre-knowledge about the relative sensitivity of the transmitter/receiver arrangement to eddy currents in the first and second objects can be obtained, and in such case the anomaly can be attributed to the object with the higher sensitivity. An example of such pre-knowledge is the relative or absolute spacing of the transmitter/receiver arrangement from each of the objects, wherein the sensitivity is typically higher for the closer object. Another example is that the probe has a more sensitive side, and it is known that the more sensitive side faces one of the objects. Such knowledge can for example be obtained from video or sonar equipment monitoring the probe orientation at the measurement position, or from an orientation sensor mounted on the probe.

A particular type of anomaly that can be studied is a wall thickness anomaly, which is a deviation of the wall thickness from a norm. Such a wall thickness anomaly can be caused by corrosion.

Except for a qualitative or semi-quantitative indication of an anomaly, the anomaly can also be quantified, such as a wall thickness indication, absolute or relative to the norm. If the distance of the transmitter/receiver arrangement to each of the first and second objects is known, these can be used in the quantification.

In a preferred embodiment, the transmitter/receiver arrangement is provided with a fixation means, which is operated to fix the transmitter/receiver arrangement at a measurement position with respect to the assembly at least during activating of the device. Movements of the probe with the transmitter/receiver arrangement during the measurement can disturb the measurements. Accordingly, there is also provided a device for detecting an anomaly in an assembly of a first and a second object forming an intermediate space between them, the device comprising a transmitter/receiver arrangement for generating an electromagnetic field, and for measuring a signal indicative of an eddy current which is generated in the assembly by the electromagnetic field; and wherein the device further comprises a fixation means which is arranged to fix the transmitter/receiver arrangement at a measurement position with respect to the assembly.

For remote operation of the probe, such as on a wireline in an annulus of a well completion, the fixation means is used to firmly locate the probe at the measurement position. A suitable way is to arrange and operate the fixation means such that it to bears the transmitter/receiver arrangement against both of the first and second objects. The fixation means can in particular comprise a resilient member, which is operated to press the transmitter/receiver arrangement against one of the first and second objects, and away from the other object. The resilient member can in particular comprise a spring and/or an inflatable member. In a special arrangement, the resilient member can assume a retracted and an expanded position, and is moved into the expanded position for fixation. In a retracted position is easier to manoeuvre the probe to the measurement position. Alternatively or in addition the fixation means can also comprise a magnet.

BRIEF DESCRIPTION OF THE DRAWINGS

The invention will now be described by way of example in more detail, with reference to the drawings, wherein

FIG. 4 shows schematically a pulsed eddy current probe during inspection in an annulus of a well completion;

FIG. 5 shows schematically the pulsed eddy current probe of FIG. 4 enlarged;

Where like reference numerals are used in the Figures they refer to the same or similar objects.

DETAILED DESCRIPTION OF THE INVENTION

Figure 1:
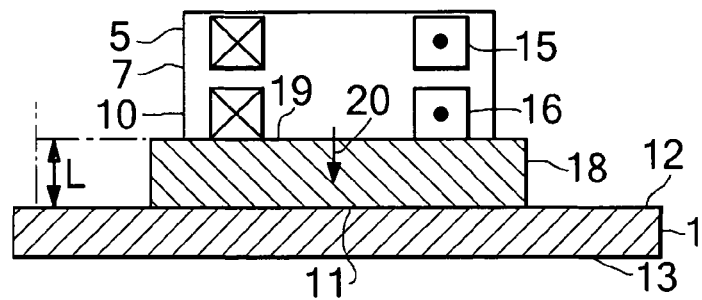
FIG. 1 shows schematically a pulsed eddy current probe arranged above an inspection object.

Eddy current methods are used for inspection of electrically conductive objects, for example to measure wall thickness. An eddy current probe, in particular a pulsed eddy current (PEC) probe, typically comprises a transmitter/receiver arrangement with a transmitter means and a receiver means. To conduct a measurement, the probe is placed in proximity with the near surface of the inspected object. The transmitter means, typically comprising an electromagnetic coil or coil arrangement, is activated, e.g. by energizing and abruptly de-energizing the coil, and this induces transient eddy currents in the object. The eddy currents give rise to a time-varying magnetic field, which generates a signal in the receiver means, typically also comprising an electromagnetic coil or coil arrangement. Often, the received signal is measured as a function of time after the transmitter pulse. Analysis of the signal yields information about anomalies in the inspected object, e.g. wall thickness variations can be measured, cracks or surface defects can be located. Examples of prior art methods are discussed in patent publications EP 321 112 A1, EP 1311800 A1, EP 1311842 A1, EP 1311843 A1, EP 1478899 A2, EP 1576335 A2.

Commonly, the probe is brought in proximity with an outer surface of an inspected object, and sufficient distance is kept from any further electrically conductive objects, because eddy currents generated therein would also be picked up by the receiver. This can be the case if metal objects are present within about 10 times the characteristic length of the transmitter/receiver arrangement, in particular within 5 times the characteristic length. The characteristic length is the length that determines the sensitive range of the transmitter/receiver arrangement, if parameters such as number of coil windings and energizing current are kept constant. In the sensitive range, eddy current measurements with a minimum signal/noise ration can be conducted. Examples of characteristic lengths will be discussed below. The characteristic length can in particular be the maximum extension of the transmitter/receiver arrangement.

In the method of the invention, the probe is typically placed at a measurement position in an intermediate space between two objects, wherein the distance between the probe and each of the objects is 10 times the characteristic length or less, in particular 5 times the characteristic length or less, and in many cases within 3 times the characteristic length.

Each of the two objects is electrically conductive, in particular from a ferromagnetic metal, in particular steel such as carbon steel. Typical inspected objects are not from stainless or austenitic steel. The objects can be covered by e.g. a non-electrically conductive material such as a polymer, glass, paint, concrete or wood, or by a thermal insulation. Typically, each object has a thickness of at least 2 mm, in particular at least 4 mm, more in particular at least 8 mm. Transient eddy current signals from carbon steel objects with such thickness gives rise to signals that are detectable for tens to hundreds of milliseconds, and diffusion of eddy currents through the material can be detected at characteristic times in the order of tens of milliseconds. Also, typically the wall thickness ratio between the thicker and the thinner of the two objects at the measurement position is in the range of 1 to 5, in many cases in the range of 1 to 3. If the objects do not differ significantly in wall thickness or material, they have similar eddy current signatures.

Reference is now made to FIG. 1. FIG. 1 shows the traditional situation of inspecting a single inspection object 1 of electrically conductive material, e.g. carbon steel. The inspection object can for example be a tubular, a plate, or a wall of a container. A pulsed eddy current probe 5 comprising a transmitter/receiver arrangement 7 is arranged in a measurement position 10 with respect to an inspection location 11 on the surface 12 nearest to the probe (the near surface) of the object 1. The transmitter/receiver arrangement 7 as shown includes separate transmitter means 15 and receiver means 16, both of which are indicated as a coil. They can also be formed by one and the same coil. It is also possible that transmitter and/or receiver means comprise a plurality of coils.

The geometric dimension mainly determining the sensitive range of the probe is the diameter of the transmitter coil 15. This diameter is the characteristic length of the probe 1.

The transmitter coil 15 is connected to a device (not shown) for energizing the transmitter coil, and the receiver is connected to a device (not shown) for recording the signals from the receiver.

The position 10 shown here is characterised by the lift-off L, parallel to the surface 12, which is realized here by arranging an electrically non-conductive object 18 such as a plastic plate ("shim") between the transmitter/receiver arrangement 7 and the inspection object 1. The thickness of the object 1 between near surface 12 and far surface 13 of the object at the inspection location 11 is for example to be measured.

The transmitter/receiver arrangement 7 has a measurement side 19 and a measurement direction indicated by the arrow 20, in the direction of the inspection object 1 during normal operation.

Figure 2:
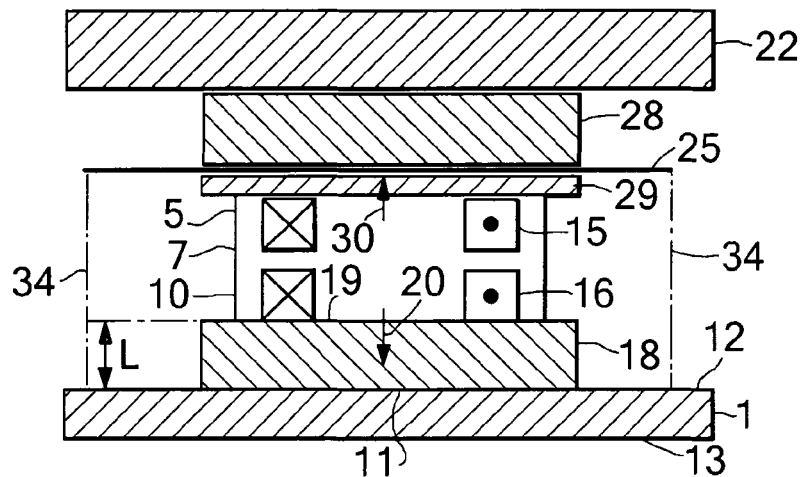
FIG. 2 shows schematically a passively shielded pulsed eddy current probe arranged between a first and a second object.

FIG. 2 shows the arrangement of FIG. 1 in a situation, according to the present invention, that a second object 22 of electrically conductive material is present in the vicinity of the inspection object (first object) 1. In the situation shown in FIG. 2 the second object 22 is substantially parallel with the first object 1. It will be understood that this is also the case for an arrangement of an inner and outer tubular of substantially parallel axes. Substantially parallel means for example within 10 degrees deviation. In the invention the transmitter/receiver arrangement is placed in the space 23 intermediate between the two objects 1,22. One could try to inspect the object 1 from the side of surface 13 by placing the transmitter/receiver arrangement there. This is however not always possible, for example when the object 1 is (part of) a tubular through which a fluid passes under process conditions.

Figure 3:
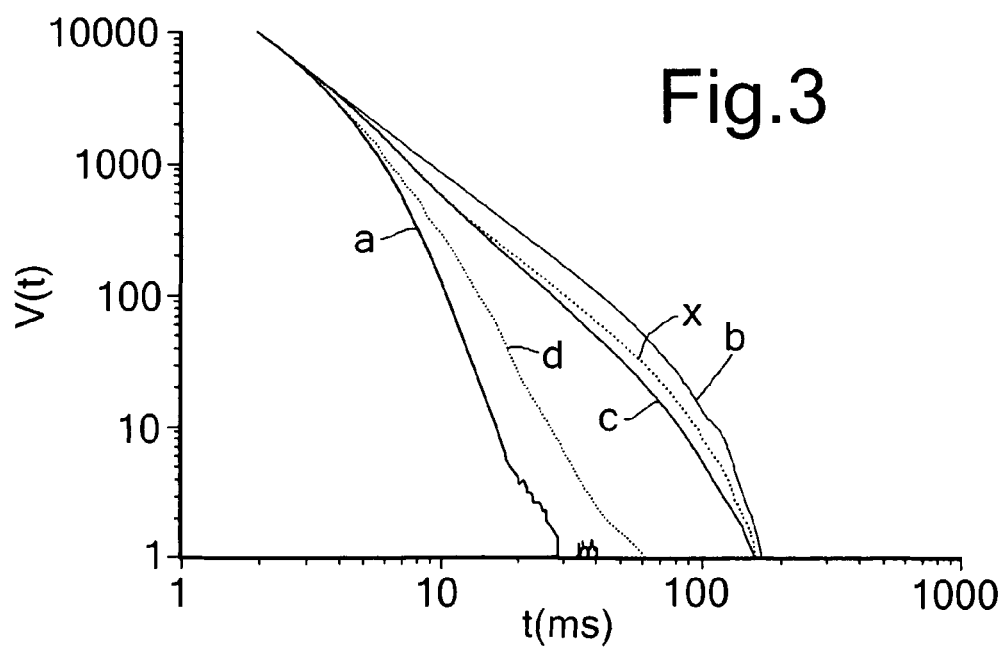
FIG. 3 shows several normalized voltage signals V(t) of the receiver as a function of time t.

Experimental results obtained in the configurations of FIGS. 1 and 2 will now be discussed with reference to FIG. 3. FIG. 3 shows voltage curves received by the receiver coil 16 as a function of time after the transmitter has been switched off. All curves have been normalized at the maximum amplitude and are displayed in arbitrary units.

Curves labelled "a" and "b" in FIG. 3 were obtained in the setup of FIG. 1 with a 4 mm and a 20 mm carbon steel test plate as inspection object 1, respectively. The plastic shim 18 was 21 mm thick and plastic shim 28 was 25 mm thick. Curve "a" breaks downwardly earlier than curve "b", in agreement with the difference in wall thickness.

Curve "c" was recorded with the PEC probe sandwiched between the 4 mm test plate as inspection object (first object) 1 and the 20 mm test plate as second object 22 in the setup displayed in FIG. 2, but without the mu-metal sheet 25 present. Curve "c" decays intermediate between curves "a" and "b", so if a wall thickness would be deduced from PEC signal "c", it would range between 4 mm and 20 mm.

Curve "x" is a superposition of the signals "a" and "b" recorded on the 4 mm and 20 mm samples, and was calculated as a superposition of the voltage curves "a" and "b" as a function of time t, $V_a(t)$ and $V_b(t)$, i.e. $V_x(t)=\alpha V_a(t)+\beta V_b(t)$. The scalar parameters $\alpha$ and $\beta$ were varied so that curve "x" best matches curve "c". It is observed that curve "x" approximates curve "c". This implies that the PEC signal recorded in between the two test plates is approximately a superposition of the signals recorded on each plate separately. Parameters $\alpha$ and $\beta$ will depend on the distances between the PEC probe and the two plates. If the distance of the transmitter/receiver arrangement to each of the first and second objects is known, it can be used in the quantification of the anomaly. With precise calibration it is in principle possible to deconvolute the responses and unravel the contributions from each of the two objects, so for each of the objects deviations from an individual norm can be detected. This is however not needed in many cases, a qualitative indication that the combined signal "c" deviates from a norm can be sufficient.

The eddy current probe of the present invention is preferably a transient or pulsed eddy current probe, i.e. generating a transient electromagnetic field in the inspected assembly, and measuring a parameter of an eddy current which is generated therein by the transient electromagnetic field, although a conventional continuous-wave eddy current probe can in principle also be used. In a continuous-wave eddy current probe a steady-state response of the inspected object is measured in response to a non-static electromagnetic field in the form of a continuously alternating electromagnetic field. A pulsed eddy-current probe is more sensitive than a conventional continuous-wave eddy current probe.

A particular use of the present invention is in the inspection of completions of hydrocarbon (oil and/or gas) wells. Such completions typically include concentric steel pipes, referred to as conductors, casing, or tubing. The completion extends from a downhole position inside the wellbore to the wellhead, which can be at land, or in offshore installations at a platform. Several parts of the completion can be subject to corrosion. In offshore installations for example, sea water can be present in an outer annulus of a completion, such as between a conductor and the outer casing. Corrosion sensitive areas are at sea level, where tidal effects and waves cause exposure of the well completion to water and air, or in a so-called splash zone even to aerated water. There is a need to perform inspection of inner tubulars. Oftentimes the only practical access path is through the annulus.

Reference is made to FIG. 4 which shows schematically the inspection of a well completion 40 from inside annulus 42 between concentric tubulars. Here, parts of two carbon steel tubulars of the well completion 40 are shown, outer tubular (conductor) 44 (shown partly cut open), and inner tubular (casing) 46. It will be understood that in case of more tubulars another annulus can be inspected. For example, the probe can be inserted in either the 'D' annulus between conductor and surface casing, the 'C' annulus between surface casing and intermediate casing, the 'B' annulus between intermediate casing and production casing or the 'A' annulus between production casing and production tubing. Entry into the 'D' annulus permits inspection of the conductor and surface casing, the 'C' annulus enables to inspection of the surface casing and intermediate casing. Entry into the 'D' annulus is possible at the gap between bottom of the well head and top of the conductor. Entry into the 'C', 'B' and 'A' annulus requires opening of site arm valves and inserting the probe through these valves.

Typical dimensions for a conductor are from 60 to 90 cm, in particular 76 cm (30") diameter and from 20 to 30 mm, in particular 25 mm wall thickness, and for a surface casing from 40 to 60 cm, in particular 51 cm (20") diameter and from 8-20 mm, in particular 12 mm wall thickness.

A PEC probe 50 is deployed at a wireline, cable, or umbilical 53 from the wellhead (not shown), e.g. at an offshore platform, into the annulus 42. At the lower end of the probe, weights 55 are mounted. Transverse elastic whiskers 58 (of which only one is visible in FIG. 4) are mounted to prevent rotation of the probe in the annulus 42.

When the cable, wireline, or umbilical 53 is fastened at the top, resilient fixation means presses the probe onto the first object, outer tubular 44, and preferably as shown at the same time away from the inner tubular 46 (second object). In this way the transmitter/receiver arrangement is fixed by bearing against the casing and the conductor at the same time.

The Figure shows a resilient fixation means in the form of spring loop 60. More springs/spring loops can be arranged, extending into different radial directions. It is also possible to use an inflatable member such as a bellows instead of or in addition to the spring(s) 60. The spring and/or the bellows can be arranged in a retracted position while the probe is moved to an inspection position, and released or inflated there, e.g. remotely operated via the cable 53.

The fixation means in this example realizes an orientation of the probe towards one of the objects; the probe is pushed onto the conductor and away from the casing, further minimizing influences from the casing on the measurements.

A further fixation can be provided as shown here by magnet 63, the strength of which is selected such that the probe is still pulled downwards by the weights 55 when the cable 53 is loose.

The fixation means in this example realizes an orientation of the probe towards one of the objects; the probe is pushed onto the conductor and away from the casing. So, the signal will be dominated by the contribution from the conductor.

A video camera 66 is mounted on the cable, wireline, or umbilical 53 so that the probe can be monitored during its decent into the annulus. In this way the orientation of the probe towards either the casing or the conductor can be checked. Alternatively, a sonar device can be used instead of or in addition to the video camera, in situations where visual inspection is not possible such as when the annulus is filled with a liquid such as oil or sea water. It is also possible to mount an orientation sensor such as a gyroscope on the probe to obtain orientation information.

The cable, wireline, or umbilical 53 has several functions. Next to the function of supporting and guiding the probe 50 it also provides necessary electrical connections to and from the probe (including power supply, control, operation and data transmission), to and from the video camera, and suitably also electrical, pneumatic or hydraulic connections for operating a fixation means such as a releasable spring, in-/deflatable bellows.

FIG. 5 shows an enlarged schematic view of the interior of probe 50 of FIG. 4. The transmitter/receiver arrangement 70 of the probe differs from that discussed with reference to FIGS. 1 and 2. The transmitter coils 72,73 and receiver coils 75,76 are arranged on a U-shaped ferrite yoke 79. The magnetic field produced by the transmitter coils is guided to the poles 81,82 of the yoke, at the measurement side 84 of the probe. The field generated by the eddy currents in an inspected object at the measurement side 84 is guided to the receiver coils 75,76. Transmitter and/or receiver coils could also be arranged on the legs of the U-shaped yoke 79.

The probe is mounted in a housing 87. A plastic spacer 89 of e.g. 10 mm thickness is arranged at the measurement side, to provide a constant lift-off. For the sake of clarity, electrical connections and external parts of the probe are not shown.

The total thickness of the probe excluding the plastic spacer can typically be in the order of 10-40 mm. An annulus or intermediate space of e.g. 100 mm or less, such as 70 mm or less, can be inspected.

The PEC probe shown here is functionally similar to that described in EP 910784 A1, incorporated herein by reference, in that it is a so-called focused probe. When the transmitter coils 72,73 are connected in series, together with the yoke 79 they represent two laterally spaced-apart emitters for emitting an electromagnetic field, so driven that the resulting electromagnetic field in the central region, between the poles 81,82, is intensified. The characteristic length of the probe 50 determining its sensitive range is the pole spacing, i.e. the distance between the centres of the poles 81,82. It is also the maximum dimension of the transmitter/receiver arrangement. The characteristic length can suitably be in the range of from 10 mm to 200 mm, in particular of from 20 mm to 150 mm.

The U-shaped yoke has the further effect that there is a significantly higher sensitivity of the probe towards the measurement side 84 than to the opposite side, unlike for example the simple probe 1 of FIGS. 1 and 2.

During normal operation the probe 50 is lowered into the annulus 42, whereby the probe is mainly pulled downwards by the gravity force of weights 55 rather than pushing it by the cable 53.

By means of the camera 66 the correct orientation can be verified, and obstructions in the annulus can be spotted. The camera can also signal a situation that the annular distance between surface casing and conductor varies, because the tubulars are misaligned and are not concentric anymore, and this can be taken into account when in the interpretation of the measurements. It is known that varying lift-off has an influence on the signals. If the lift off does not significantly vary, it is easier to quantify the measurements and attribute changes in the signal to an anomaly in the metal objects.

When the probe 50 has arrived at a measurement position, the cable 53 is fixed, and the probe 50 is fixed in position by the combined action of spring loop 60 and magnet 63, both pressing the probe against the wall of the conductor 44, so that it remains stationary when the probe is activated.

Energizing the transmitter coils with a current pulse is done from surface via cable 53, and the signal picked up by the receiver is transmitted to surface where it can be processed to determine an anomaly. Suitably inspection is carried out at a plurality of measurement positions, in this way relative differences can be compared, and an internal norm can be established from e.g. a suitable average of a parameter from the plurality of measurement positions. It is also possible to measure a reference signal at one or more measurement positions where there is no anomaly, that can serve to determine a norm.

Since in the present situation pre-knowledge is available about the close spacing of the probe to the conductor and the orientation of the measurement side of the probe towards the conductor, and moreover the conductor has a larger nominal wall thickness, a detected anomaly can be attributed to the conductor. Clearly, inspection can also be done preferentially for contributions from the inner tubular 46, in which case the probe can be used analogously, but rotated by 180 degrees.

In order to decrease or substantially suppress the influence of the eddy current response from one of the objects on the measurements, it is possible to use a shielded eddy current probe comprising a magnetic shield means, which provides at least a partial magnetic shield for the transmitter/receiver arrangement in a direction other than the measurement direction. The magnetic shield means can in particular comprises a piece of ferromagnetic material, preferably selected from the group consisting of a ferromagnetic alloy and a ceramic, most preferably mu-metal.

Figure 6:
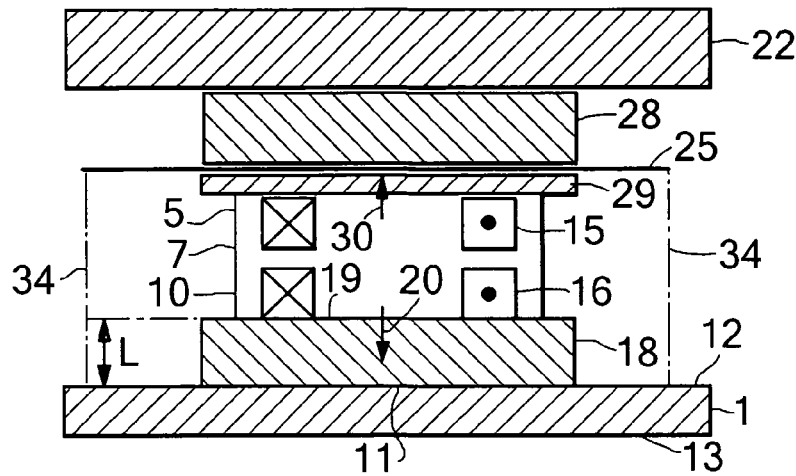
FIG. 6 shows schematically a passively shielded pulsed eddy current probe arranged between an inspection object and a further object.

FIG. 6 shows the arrangement of FIG. 1 in the situation that a further object 22 of electrically conductive material is present in the vicinity of the inspection object 1. In the situation shown in FIG. 6 the further object 22 is substantially parallel with the inspection object 1. It will be understood that this is also the case for an arrangement of an inner and outer tubular of substantially parallel axes. Substantially parallel means for example within 10 degrees deviation. The transmitter/receiver arrangement is placed in the space intermediate between the two objects 1,22. One could try to inspect the object 1 from the side of surface 13 by placing the transmitter/receiver arrangement there. This is however not always possible, for example when the object 1 is (part of) a tubular through which a fluid passes under process conditions. The challenge is therefore to inspect the inspection object 1 from the intermediate space while suppressing or minimizing the influence of the further object 22 on the measurements.

In one embodiment, this is achieved in the invention by arranging a magnetic shield between the transmitter/receiver arrangement and the further object, which shield in the embodiment of FIG. 6 takes the form of a ferromagnetic sheet 25. Further plastic shims 28 and 29 are arranged as spacers. The ferromagnetic sheet provides a magnetic shield for the transmitter/receiver arrangement in a direction 30 other than the measurement direction 20, in this case opposite to the measurement direction.

Preferably the ferromagnetic sheet is from mu-metal, as it can be for example obtained from Mu-Shield Inc. (Goffstown, N.H., USA) as MIL N 14411C COMP 1. Mu-metal is an alloy of mainly Nickel (in the order of 75-82% and Iron (in the order of 13-20 wt %), and further one or more other metals such as molybdenum, cobalt, copper, chromium. The relative magnetic permeability of mu-metal is very high, exceeding 104, and even 105. Experiments have been conducted with thicknesses of 0.09, 0.15, 0.23 and 1.56 mm, and even for 0.09 mm good shielding was observed. So it is believed that even thinner mu-metal sheets can be suitable, such as 0.01 mm thick. Thicker sheets can also be used, but may not be practical in compact probes. Ferrite, or other ferromagnetic materials can in principle also be used, but typically larger thicknesses are required.

It is noted that in conventional design of an eddy current probe, with the exception of a yoke optionally extending through the coil(s), one uses only non-ferromagnetic materials in the vicinity of the transmitter-receiver arrangement, so as to not disturb the magnetic fields transmitted to and from the inspection object. A normal design rule is that no ferromagnetic materials should be present near the transmitter/receiver arrangement within one characteristic diameter of the transmitter/receiver arrangement, such as the diameter of a transmitter or receiver coil. In particular no ferromagnetic materials which are electrical conductors should be present. The magnetic shield of the present invention is placed (much) closer to the transmitter. It has been found, however, that the measurements at the measurement side are not substantially disturbed by the presence of a shield of mu-metal or ferrite, if the shield is properly fixed against movement. It is believed that this is due to the fact that mu-metal has a resistivity of the order of 0.5-0.7 $10^{-6}$ $\Omega$·m, a factor of 2-4 higher than carbon steel that is typically inspected. Eddy currents that are induced in the mu-metal by a pulsed eddy current measurement are therefore dampened out fast enough in order to not disturb the measurement of a carbon steel inspection object. Also, dampening out is fastest for thin mu-metal sheets, a signal from a sheet of 0.3 mm for example has deceases to essentially zero within the dead time of the probe of typically 1-2 ms, which is the time after a transmitter pulse has been switched off and before the receiver is opened. Ferrite has a much higher resistivity, so eddy currents are hardly generated therein.

Figure 7:
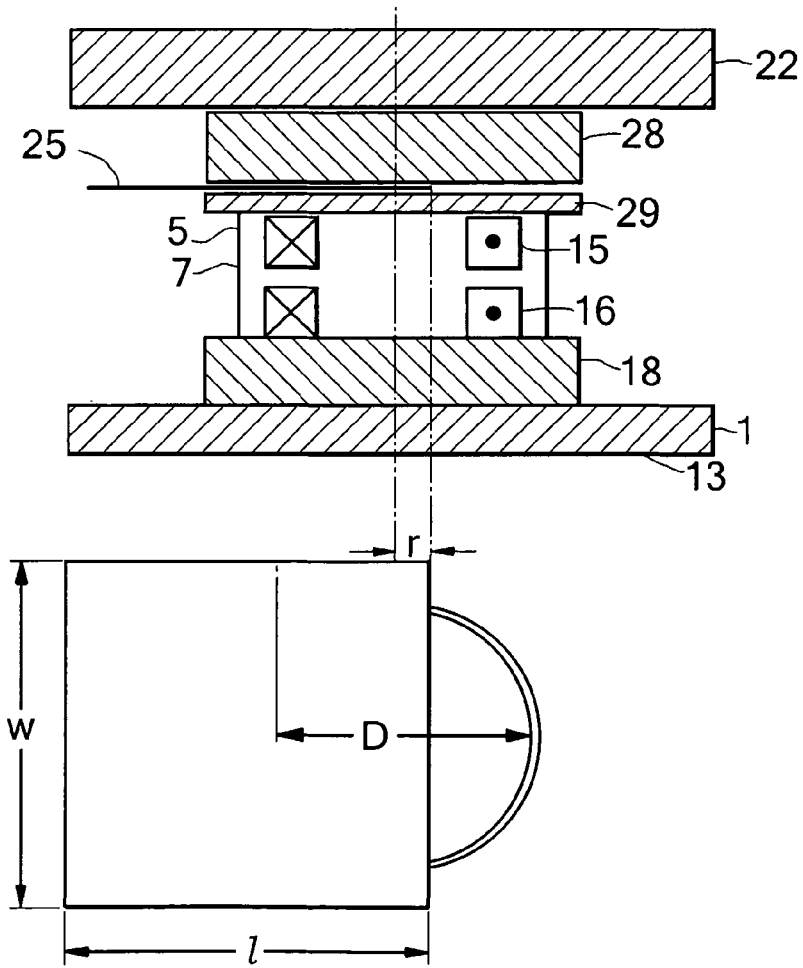
FIG. 7 shows schematically a shielded pulsed eddy current probe arranged between an inspection object and a further object, in an arrangement to study the effect of partial shielding.
Figure 8:
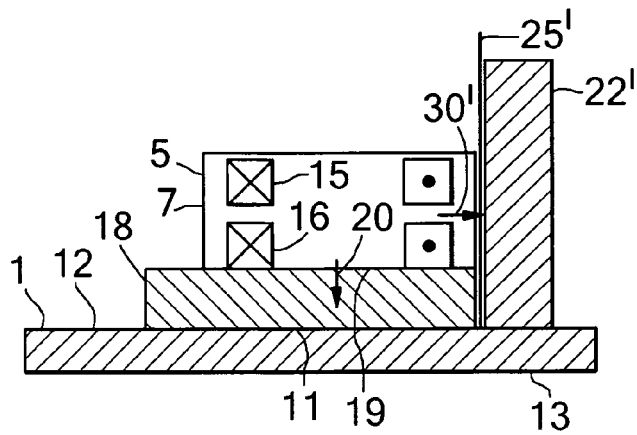
FIG. 8 shows schematically a pulsed eddy current probe and a shielding means arranged in a corner formed by an inspection object and a further object.

FIG. 7 shows a set-up used for experiments conducted in order to estimate which coverage of the transmitter/receiver arrangement with mu-metal can be effective, when the ferromagnetic shield 25 was pulled out laterally. The top view in the lower part of FIG. 8 shows the long piece of mu-metal of 0.23 mm thickness that was used for this purpose, w=85 mm wide and l=150 mm long. The distance of the edge of this mu-metal and the centre of the probe is denoted by r. The coil has a diameter of D=15 mm, so that r=−15 mm implies that the mu-metal does not cover the transmitter coil. The coil is covered for 50% in case of r=0 mm and 100% when r=15 mm. It was found that for a sufficient shielding effect preferably at least 50% of the surface area of the transmitter coil facing the further object should be covered, which is in the embodiment of FIG. 7 equivalent to the cross section of the transmitter/receiver arrangement facing the other object 22. For r>15 mm the shielding was not found to significantly improve.

If desired, a magnetic shield in the form of a ferromagnetic diaphragm can be placed between the transmitter/receiver arrangement 7 and the inspection object 1, i.e. a ferromagnetic sheet having an opening, suitably of about the diameter of the transmitter/receiver arrangement 7 and aligned therewith.

It can also be desirable to provide a lateral shield around the transmitter/receiver arrangement 7, which is indicated as an optional ring 34 in FIG. 6, in order to shield against magnetic fields laterally.

Lateral magnetic shielding was found effective when the inspection object and the further object were in a different, non-parallel configuration.

The invention is clearly not limited to inspecting an assembly of substantially parallel objects. Also objects having much larger angle between the surfaces facing towards the intermediate space between them can be inspected FIG. 5 shows the situation that the further object 22' is perpendicular to the inspection object, and that measurements are to be performed close to the corner formed by the two objects 1 and 22'. It was found that effective shielding can be achieved by a mu-metal sheet 25' between the further object and the transmitter/receiver arrangement, in front of the further object 22' as shown. The shield 25' is perpendicular with respect to the inspection object and parallel with the measurement direction 20, so the magnetic shield provides shielding in perpendicular direction 30' to the measurement direction 20.

It can be useful for general purpose use to provide a magnetic shield at all sides around the probe, except at the measurement side 19 in the active measurement area of the probe towards the inspection object.

The magnetic shield can form an integral part of the probe, or it can be a removable part that is separately placed after the probe was arranged in a measurement position with regard to the inspection object, in which case the probe and the shield form an assembly.

The eddy current probe of the present invention is preferably a transient or pulsed eddy current probe, i.e. generating a transient electromagnetic field in the inspection object, and measuring a signal indicative of an eddy current which is generated in the inspection object by the transient electromagnetic field, although a magnetic shield can in principle also be used in a conventional continuous-wave eddy current probe. In a continuous-wave eddy current probe a steady-state response of the inspection object is measured in response to a non-static electromagnetic field in the form of a continuously alternating electromagnetic field. It is believed that the ferromagnetic shield, in particular a mu-metal shield, is more effective in suppressing transient magnetic fields than in a steady-state situation. Moreover, a pulsed eddy-current probe is more sensitive than a conventional continuous-wave eddy current probe.

Figure 9:
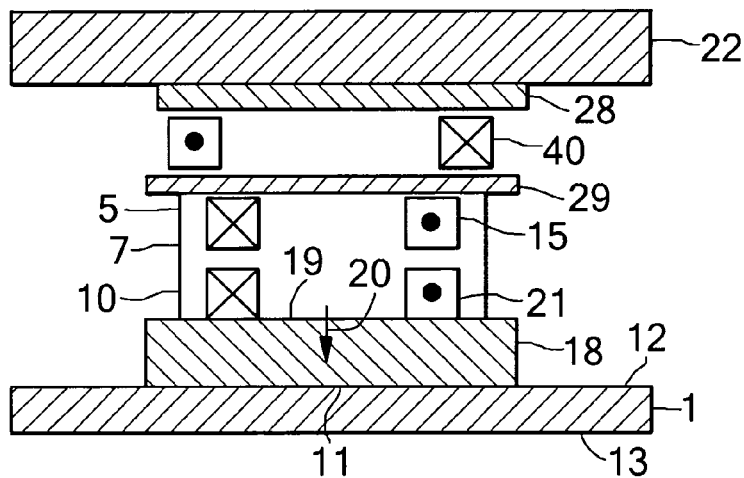
FIG. 9 shows schematically an actively shielded pulsed eddy current probe arranged between an inspection object and a further object.

Reference is made to FIG. 9 showing another embodiment in which the magnetic shield means comprises an active magnetic shield means, electromagnetic shielding transmitter in the form of shield coil 40. The shield coil is suitably set up such that it is activated together with the transmitter coil, and such that current flows in opposite direction compared to the transmitter coil. So, a magnetic field opposite to that of the transmitter is created. The geometry of the coils and currents can be adjusted such that at the side of the probe facing the further object 22, a substantial or full compensation of the transmitter magnetic field can be achieved. Because of the larger distance to the shield coil, at the measurement side there is caused only a limited decrease of the magnetic field generated by the transmitter coil.

The inspection object and the further object are electrically conductive, in particular from a ferromagnetic metal, in particular steel such as carbon steel. Typical inspected objects are not from stainless or austenitic steel. The objects can be covered by e.g. a non-electrically conductive material such as a polymer, glass, paint, concrete or wood, or by a thermal insulation. Typically, each object has a thickness of at least 2 mm, in particular at least 4 mm, more in particular at least 8 mm. Transient eddy current signals from carbon steel objects with such thickness gives rise to signals that are detectable for tens to hundreds of milliseconds, and diffusion of eddy currents through the material can be detected at characteristic times in the order of tens of milliseconds. Also, typically the wall thickness ratio between the thicker and the thinner of the two objects at the measurement position is in the range of 1 to 5, in many cases in the range of 1 to 3. If the objects do not differ significantly in wall thickness or material, they have similar eddy current signatures. The inspection object and the further object can both be parts of the same, larger, object.

A particular use of the present invention is in the inspection of completions of hydrocarbon (oil and/or gas) wells. Such completions typically include concentric steel pipes, referred to as conductors, casing, or tubing. The completion extends from a wellhead downwardly into the wellbore. The wellhead can be at land, or in offshore installations at a platform. Several parts of the completion can be subject to corrosion. In offshore installations for example, sea water can be present in an outer annulus of a completion, such as between a conductor and the outer casing. Corrosion sensitive areas are at sea level, where tidal effects and waves cause exposure of the well completion to water and air, or in a so-called splash zone even to aerated water. There is a need to perform inspection of inner tubulars. Oftentimes the only practical access path is through the annulus.

Figure 10:
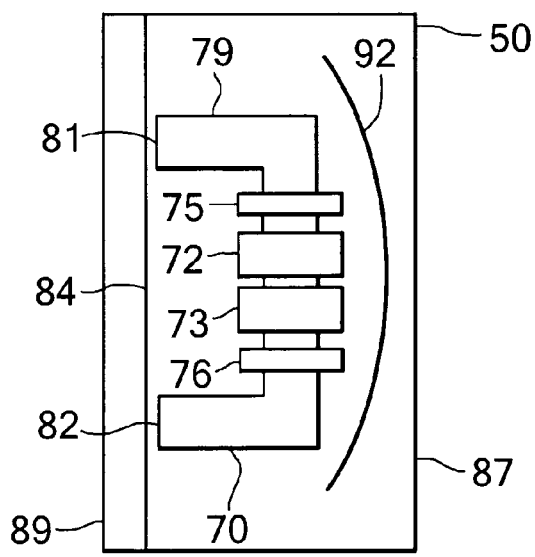
FIG. 10 shows schematically the pulsed eddy current probe of FIG. 7 enlarged.

The magnetic shield means can be an integral part of the probe as shown in FIG. 10, but it can also be separately arranged or retrofitted on an unshielded probe. It is important that the shield means is mechanically fixed with respect to the transmitter/receiver arrangement, since relative motion during pulsed operation could otherwise disturb the measurements.

Each of the two objects is electrically conductive, in particular from a ferromagnetic metal, in particular steel such as carbon steel. Typical inspected objects are not from stainless or austenitic steel. Typically, each object has a thickness of at least 2 mm, in particular at least 4 mm, more in particular at least 8 mm. Transient eddy current signals from carbon steel objects with such thickness gives rise to signals that are detectable for tens to hundreds of milliseconds, and diffusion of eddy currents through the material can be detected at characteristic times in the order of tens of milliseconds. Also, typically the wall thickness ratio between the thicker and the thinner of the two objects at the measurement position is in the range of 1 to 5, in many cases in the range of 1 to 3. If the objects do not differ significantly in wall thickness or material, they have similar eddy current signatures. The inspection object and the further object can both be parts of the same, larger, object.

Figure 11A:
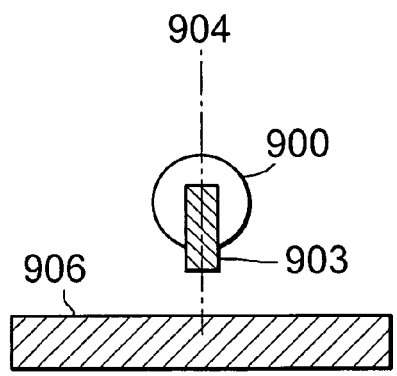
FIG. 11a shows a front view of the pulsed eddy current probe in a preferred orientation.
Figure 11B:
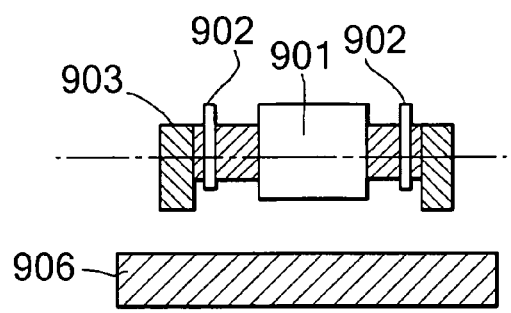
FIG. 11b shows a side view of the pulsed eddy current probe in a preferred orientation.

In one embodiment, the pulsed eddy current probe further comprises an orientation sensor, which can be used to measure the position of the probe with respect to the object it is measuring. Up until this point in the application, orientation has been discussed to indicate generally whether or not the probe is pointed at the inspection object or a further object within the vicinity of the inspection object. From this point forward, a more refined measurement of orientation will be discussed referring to a precise measurement of position of the probe with respect to the object it is measuring (e.g. deviation from a preferred position). FIGS. 11A and 11B schematically display a PEC probe 900, with one transmitter coil 901, two receiver coils 902 and a ferrite yoke 903.

The probe has a measurement direction which is perpendicular to the surface of inspection object 906 when the device is situated in a preferred orientation. The probe has a device axis, which is perpendicular to the surface of inspection object 906. The orientation receiver coil arrangement (in this embodiment 901 and 902) defines another axis which is perpendicular to the device axis and the measurement direction. When the probe is situated in a preferred orientation, the orientation receiver coil arrangement is arranged symmetrically with respect to the device axis.

Figure 11C:
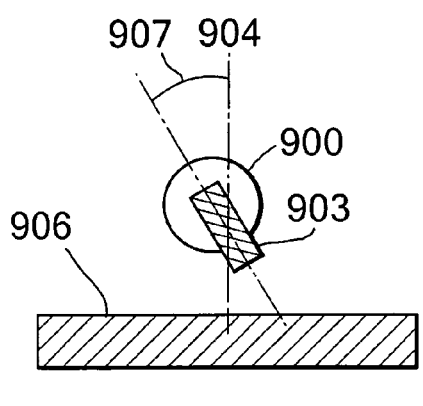
FIG. 11c shows a front view of the pulsed eddy current probe in a rolled or tilted orientation.
Figure 11D:
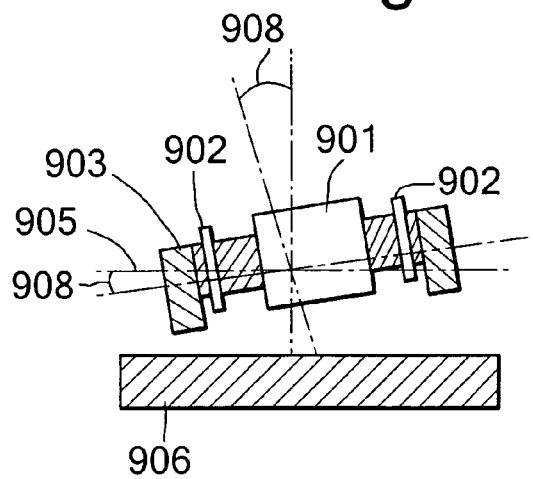
FIG. 11d shows a side view of the pulsed eddy current probe in a rolled or tilted orientation.

Often it is not easy to guarantee such an orientation, and probe 900 may be tilted and rolled with respect to the preferred orientation. In FIG. 11, the probe is arranged on a coordinate system having a short axis 904 perpendicular to the surface of inspection object 906 and a long axis 905 parallel to the surface of inspection object 906. FIGS. 11C and 11D show probe 900 in a tilted or rolled orientation. In this situation, the probe may be used to measure a deviation angle from the preferred orientation by detecting rotation about the device axis. The roll angle 907 is defined as the probe's deviation from the short axis and is shown in FIG. 11C. The tilt angle 908 is defined as the probe's deviation from the long axis and is shown in FIG. 11D.

The reading from a pulsed eddy current measurement is dependent on the orientation of the probe with respect to the inspection object. Measurements taken at different times and/or locations on the measurement object can be best compared when they were taken with the probe in the same orientation. By monitoring the orientation, such as by monitoring roll and/or tilt angles with an orientation sensor, one can adjust the position of the probe and obtain a more accurate and/or better comparable measurements of the inspection object.

Figure 12A:
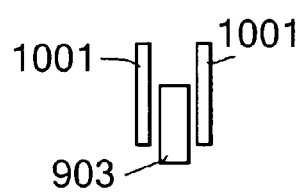
FIG. 12a shows a front view of one embodiment of the pulsed eddy current probe featuring an orientation sensor.
Figure 12B:
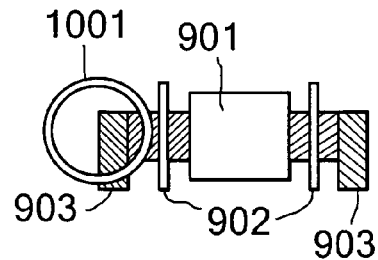
FIG. 12b shows a side view of one embodiment of the pulsed eddy current probe featuring an orientation sensor.

FIGS. 12A and 12B show an embodiment of the pulsed eddy current probe with an orientation sensor 1001. In the embodiment shown, orientation sensor 1001 comprises an orientation sensor arrangement comprising two orientation receiver coils. However orientation sensor 1001 may comprise a single receiver coil or more than one receiver coils. Alternatively orientation sensor 1001 could also be any other known known sensing method for example a gyroscope.

Figure 13A:
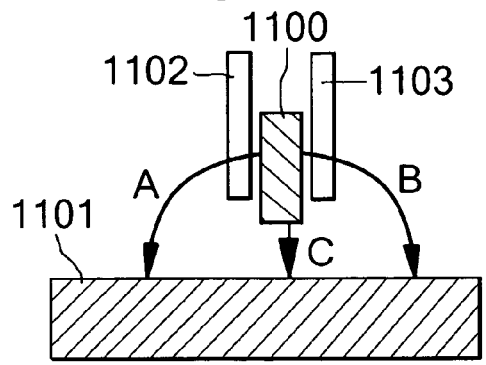
FIG. 13a displays the magnetic flux through the orientation receiver coils when the probe is positioned normally.
Figure 13B:
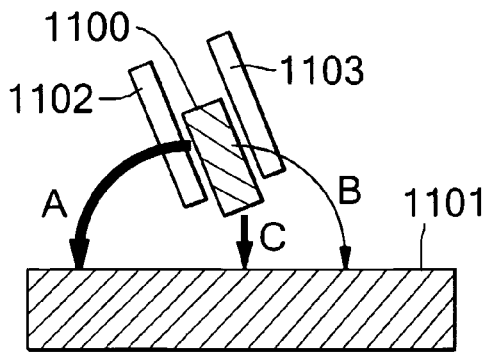
FIG. 13b displays the magnetic flux through the orientation receiver coils when the probe is rolled.

FIGS. 13A and 13B illustrate the principle of operation of one embodiment of the orientation sensor. FIG. 13A shows probe 1100, inspection object 1101, first orientation receiver coil 1102 and second orientation receiver coil 1103. Schematically the change in magnetic field of the eddy currents induced in inspection object 1101 is shown after the transmission coil has been switched off. The change in magnetic flux through first orientation receiver coil 1102 is equal to that through second orientation receiver coil 1103. When the probe rolls to the left, as shown in FIG. 11B, the change in flux through first orientation receiver coil 1102 is no longer equal to the change in flux through second orientation receiver coil 1103. This is because the magnetic flux increases with decreasing distance of coil to the inspection object.

In the case where the orientation receiver arrangement comprises more than one orientation receiver coil, there are multiple options for wiring. In a preferred embodiment using two orientation receiver coils, the two coils are arranged along a common axis and are wired together to form a combined normal coil. When the two coils are arranged symmetrically with respect to the device axis as shown in Figure xxx, the total magnetic flux through the coil arrangement is zero, when the probe is oriented such that its measuring direction is perpendicular to the surface of the inspection object. The output from the orientation receiver arrangement is zero. Alternatively, the orientation receiver coils may be wired such that the induced current runs in different directions in each coil, in which case the signal from the orientation receiver arrangement goes through a minimum at the perpendicular orientation.

Figure 14:
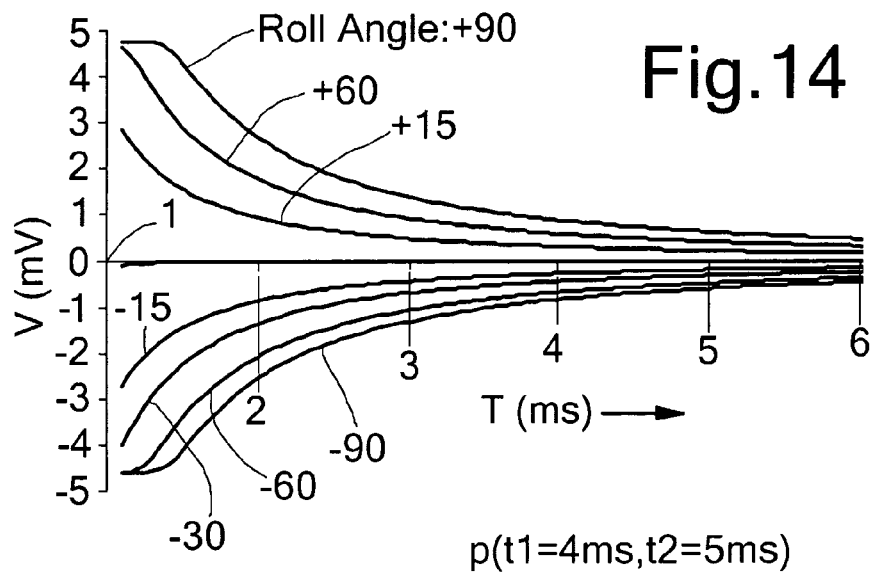
FIG. 14 displays the voltage measured over the orientation receiver coils after amplification as a function of time.

FIG. 14 displays the voltage measured over the orientation receiver coils after amplification as a function of time. The terminals of the probe were connected to an amplifier which is connected to an analogue-to-digital converter (ADC). The ADC was programmed to sample the voltage at its input at predetermined moments in time, starting when the excitation current has been switched off. Signals were recorded for different values of the roll angle. As shown in FIG. 14, the signal is close to zero when the roll angle is zero. The signal is increasingly negative for negative roll angles and increasingly positive for positive roll angles.

Figure 15:
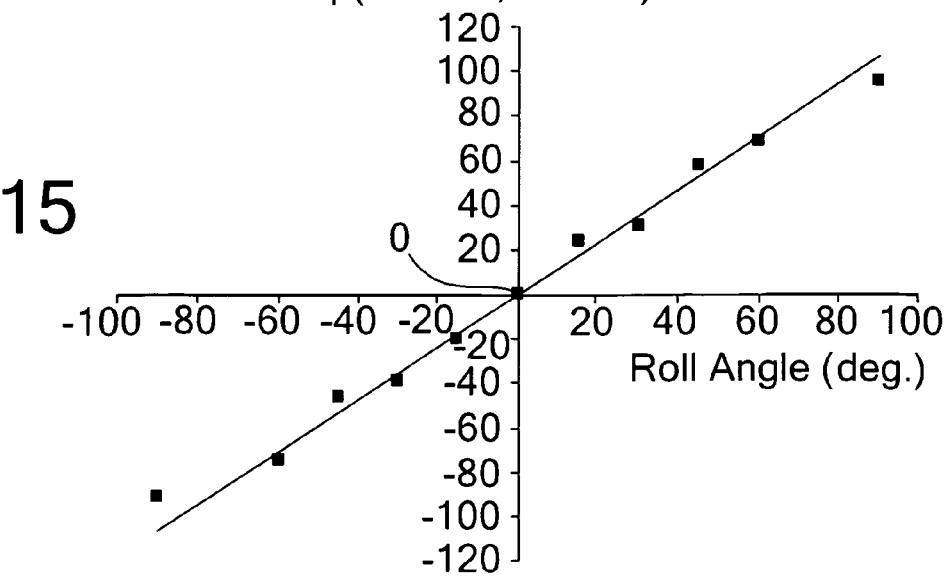
FIG. 15 displays $\rho(t1=4\ ms, t2=5\ ms)$ as a function of roll angle.

The signal strength measured over the orientation receiver coils not only depends on the roll/tilt angle, but also on the sensor lift-off or the distance between PEC probe and inspection object. It is therefore convenient to divide the signal measured over the orientation receiver coils by the signal recorded on the receiver coils for the wall thickness. An analogue-to-digital convert (ADC) is used to sample and record the voltage signals of the orientation receiver coils and wall thickness measurement coils at fixed time intervals. From the digitized signals, quantity $$\rho(t1, t2) = \frac{\sum_{i=t1}^{t2} V(i)}{\sum_{i=t1}^{t2} U(i)}.$$

is determined, where V(i) is the voltage measured on the orientation receiver coils at time i; U(i) is the voltage measured on the receiver coils at time i, t1 is a first time and t2 is a second time. The summation is over the ADC samples. The times i, t1 and t2 are since the excitation coil has been switched off. $\rho(t1=4$ ms,$t2=5$ ms) is displayed in FIG. 13 as a function of the roll angle. $\rho(t1=4$ ms,$t2=5$ ms) is dimensionless and depends on the number of turns in the orientation receiver coils and the coils for measuring wall thickness. $\rho(t1=4$ ms,$t2=5$ ms) also depends on the gains in the amplifiers. The roll angle can be determined after a calibration. In this calibration $\rho(t1,t2)$ is measured at a calibration plate for a set of known roll angles. From this, a calibration curve such as the one in FIG. 15 is determined. The roll angle at another position can subsequently be deduced by comparison to the calibration curve.

The invention is clearly not limited to inspecting an assembly of substantially parallel objects. Also objects having a larger angle between the surfaces facing towards the intermediate space between them can be inspected, such as an angle of up to 30 degrees, up to 60 degrees, or even higher. The first and the second object can both be parts of the same, larger, object.

That which is claimed is:

1. A method for detecting an anomaly in an assembly of a first tubular object and a second tubular object of electrically conductive material forming an intermediate annular space between them, the method comprising:
   providing a device comprising a transmitter/receiver arrangement for generating an electromagnetic field in an electrically conductive object, and for measuring a signal indicative of an eddy current which is generated in the assembly by the electromagnetic field;
   arranging the device in a measurement position within the intermediate annular space;
   activating the device so as to receive a signal indicative of an eddy current in the assembly; and
   comparing the signal with a norm so as to detect if an anomaly is present at the measurement position;
   wherein the transmitter/receiver arrangement is provided with a fixation means which is operated to fix the transmitter/receiver arrangement at a measurement position with respect to the assembly at least during activating of the device;
   wherein the fixation means comprises a resilient member which is operated to press the transmitter/receiver arrangement against the first object and away from the second object.

2. The method according to claim 1, wherein the first and second objects are an inner and an outer tubular with the intermediate annular space between, wherein the inner and outer tubulars form part of a well completion.

3. The method according to claim 1, further comprising the steps of obtaining pre-knowledge about the relative sensitivity of the transmitter/receiver arrangement to eddy currents in the first and second objects, and attributing the anomaly to the object with the higher sensitivity.

4. The method according to claim 1, wherein the anomaly is a wall thickness anomaly, in particular a wall thickness anomaly caused by corrosion.

5. The method according to claim 1, wherein the anomaly is quantified.

6. The method according to claim 1, wherein the fixation means is operated to bear the transmitter/receiver arrangement against the first object and against the second object.

7. The method according to claim 1, wherein the resilient member comprises a spring and/or an inflatable member.

8. The method according to claim 7, wherein operating the resilient member comprises moving from a retracted position to an expanded position.

9. The method according to claim 1, wherein the inner and outer tubulars form part of a well completion of a hydrocarbon well.

10. The method according to claim 1, wherein the hydrocarbon well is operated so as to produce hydrocarbons from the well during or after the inspection for an anomaly in the well completion.

11. The method according to claim 1, further comprising: at least one orientation sensor arranged on the device to provide at least one output value; wherein the at least one output value allows to detect whether the device is arranged in a preferred orientation.

12. The method of claim 11, wherein the at least one orientation sensor comprises an orientation receiver coil arrangement comprising at least one orientation receiver coil.

13. The method according to claim 12, wherein the device has a device axis perpendicular to the measurement direction, wherein the orientation receiver coil arrangement defines an axis perpendicular to the device axis and to the measurement direction, preferably wherein the orientation receiver coil arrangement is arranged symmetrically with respect to the device axis.

14. A device for detecting an anomaly in an assembly of a first tubular object and a second tubular object forming an intermediate annular space between them, the device comprising a transmitter/receiver arrangement for generating an electromagnetic field, and for measuring a signal indicative of an eddy current which is generated in the assembly by the electromagnetic field; and wherein the device further comprises a fixation means which is arranged to fix the transmitter/receiver arrangement with respect to the assembly at a measurement position within the intermediate annular space;

wherein the fixation means comprises a resilient member arranged to press the transmitter/receiver arrangement against the first object and away from the second object.

15. The device according to claim 14, wherein the fixation means is arranged to bear the transmitter/receiver arrangement against the first object and against the second object.

16. The device according to claim 14, wherein the resilient member comprises a spring and/or an inflatable member.

17. The method according to claim 1, further comprising: using at least one orientation sensor arranged on the device to provide at least one output value that is indicative of a deviation from a preferred orientation of the device with respect to the inspection object.

18. The method according to claim 17, wherein the at least one orientation sensor comprises an orientation receiver coil arrangement comprising at least one orientation receiver coil in which an orientation signal is induced in response to transient eddy currents generated in the inspection object.

19. The method of claim 18, wherein in the preferred orientation the measurement direction is perpendicular to the surface of the inspection object, wherein the device has a device axis perpendicular to the measurement direction, wherein the orientation receiver coil arrangement defines an axis perpendicular to the device axis and to the measurement direction, and wherein the orientation signal is used to detect a deviation from the preferred orientation by rotation about the device axis.

20. The method of claim 19 further comprising adjusting the orientation of the device in response to the output value.

\* \* \* \* \*